United States Patent [19]

Christidis et al.

[11] Patent Number: 5,053,527
[45] Date of Patent: Oct. 1, 1991

[54] PROCESS FOR THE MANUFACTURE OF ALKYL PYRUVATES

[75] Inventors: Yani Christidis; Jean-Claude Vallejos, both of Paris, France

[73] Assignee: Societe Francaise Hoechst, Puteaux, France

[21] Appl. No.: 525,209

[22] Filed: May 18, 1990

Related U.S. Application Data

[63] Continuation of Ser. No. 299,692, Jan. 23, 1989, abandoned.

[30] Foreign Application Priority Data

Jan. 22, 1988 [FR] France .................. 88 00676

[51] Int. Cl.$^5$ ............................................. C07C 69/68
[52] U.S. Cl. ..................................... 560/174; 562/577
[58] Field of Search ......................... 560/174; 562/577

[56] References Cited

FOREIGN PATENT DOCUMENTS 2734207 2/1979 Fed. Rep. of Germany .

OTHER PUBLICATIONS

Patent Abstracts of Japan, vol. 10, No. 276 (C-373)[2322], Sep. 19, 1986; & JP-A-61 97247 (Mitsui Toatsu) 15-05-1986.
Patent Abstracts of Japan, vol. 10, No. 31 (C-237)[2088], Feb. 1, 1986; & JP-A-60 184 050 (Kogyo Gijutsuin) 19-09-1985.
Beilsteins Handbuch Der Organischen Chemie, vol. 3, No. 279, publ. 1921, Springer Verlag, Berlin: Hauptwerk, p. 608, lines 18-19.
IDEM, Supplement 1, p. 217, lines 59-60, p. 218, line 1, 1929.
IDEM, Supplement 2, p. 395, line 17, 1942.
Patent Abstracts of Japan, vol. 7, No. 151 (C-174)[1296], Jul. 2, 1983; & JP-A-56 62136 (Kuraray K.K.) 13-04-1983.

*Primary Examiner*—José G. Dees
*Attorney, Agent, or Firm*—Browdy and Neimark

[57] ABSTRACT

The invention provides an improved process for the manufacture of alkyl pyruvates having general formula (I):

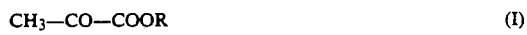

$$CH_3-CO-COOR \qquad (I)$$

where R represents a $C_1$ to $C_8$ alkyl radical, by controlled oxidation of the corresponding alkyl lactate.

The process is characterized in that the controlled oxidation is carried out using an aqueous hydrogen peroxide solution in the presence of catalytic quantities of bromium.

6 Claims, No Drawings

PROCESS FOR THE MANUFACTURE OF ALKYL PYRUVATES

This application is a continuation of application Ser. No. 07/299,692, filed Jan. 23, 1989, abandoned.

FIELD OF THE INVENTION

The present invention provides an improved process for the manufacture of alkyl pyruvates, particularly those having general formula (I):

$$CH_3-CO-COOR \quad (I)$$

where R represents a $C_1$ to $C_8$ alkyl radical.

According to this process, these pyruvates are obtained by controlled oxidation under special conditions of the corresponding alkyl lactate having general formula (II):

$$CH_3-CHOH-COOR \quad (II)$$

where R has the meaning given above.

BACKGROUND OF THE INVENTION

Products having general formula (I) are among the most important starting materials used to obtain certain molecules having interesting therapeutic properties.

Oxidation of an alkyl lactate to form the corresponding alkyl pyruvate is known either in the vapour phase using air or oxygen or in the presence of a metallic catalyst such as platinum, silver or vanadium, deposited if necessary on aluminium at temperatures of between 190° C. and 500° C., or in the liquid phase by potassium permanganate alone or mixed with copper II sulphate (see Beilsteins Handbuch der Organischer Chemie, Vol. III, 4th supplement, p. 1513).

These known processes are not entirely satisfactory, however. In particular, the catalytic oxidation reactions, although selective, are rarely complete and the chemical oxidation reactions, although complete, are either nonselective or produce substantial quantities of mineral salts.

As a result, isolation of the desired product at the end of the reaction is laborious and costly and, further, it is difficult to separate the untransformed alkyl lactate from the corresponding alkyl pyruvate by distillation given their very similar boiling points.

SUMMARY OF THE INVENTION

The inventive process for the manufacture of alkyl pyruvates having general formula (I) by controlled oxidation of the corresponding alkyl lactate overcomes these drawbacks.

The process is characterised in that said controlled oxidation is carried out using an aqueous hydrogen peroxide solution in the presence of catalytic quantities of bromine.

The aqueous hydrogen peroxide solution may be selected from various commercially available aqueous hydrogen peroxide solutions, for example. A 30% to 70% by weight, preferably 50% by weight aqueous hydrogen peroxide solution is advantageously employed.

The molar ratio of hydrogen peroxide to alkyl lactate may be between 1 and 1.2 but is preferably 1.

Bromine is used in catalytic quantities in the order of 10 to 200 mmoles per mole of alkyl lactate used. 50 to 200 mmoles of bromium per mole of alkyl lactate and preferably about 100 mmoles are advantageously used.

The process is carried out in an organic solvent which is not miscible with water, is inert towards the reactants used and in which the alkyl lactate employed is soluble.

Solvents such as dichloromethane, 1,1,1-trichloroethane and chlorobenzene may be used. Dichloromethane is advantageously used.

The reaction temperature is advantageously between 15° C. and 30° C. and preferably around 25° C. Since the oxidation reaction is exothermic, it is necessary to introduce the hydrogen peroxide slowly into the reaction medium and to cool the reaction medium in order to keep the temperature within the above limits.

The oxidation reaction may be readily followed by vapour phase chromatographic analysis of periodically taken samples.

During the oxidation reaction, small quantities of the corresponding alkyl 2-hydroperoxy-2-hydroxypropanoate may form. This is readily degraded to form the corresponding alkyl pyruvate either by heating or preferentially by treatment with a suitable reducing agent such as sodium sulphite.

At the end of the reaction, the desired alkyl pyruvate can be isolated using known means. Advantageously the two-phase reaction medium is first neutralised with sodium bicarbonate then, after decanting, the organic phase is treated with an aqueous sodium sulphite solution and, finally, after elimination of the reaction solvent, the desired alkyl pyruvate is isolated by distillation under reduced pressure.

In one embodiment, the inventive process is carried out under the influence of visible or near ultraviolet radiation of wavelengths between 250 nm and 700 nm. The inventive process is advantageously carried out in the presence of visible radiation supplied by one or more conventional incandescent lamps. The effect of the radiation is to accelerate noticeably the reaction rate without affecting the final yield.

DETAILED DESCRIPTION OF THE INVENTION

The following examples illustrate the invention without in any way limiting its scope.

EXAMPLE 1

472 g (4 moles) of ethyl lactate,
64 g (0.4 mole) of bromine
is dissolved at room temperature in 2660 g of dichloromethane in a 4 liter three-necked glass flask equipped with a thermometer and a mechanical stirring system and irradiated with a 200 Watt incandescent lamp.

272 g of 50% by weight aqueous hydrogen peroxide (4 moles) was then introduced into the stirred irradiated solution over a period of 90 minutes. The temperature of the reaction medium was kept to 25° C. by light external cooling.

The reaction medium was left, maintaining the temperature of 25° C., the irradiation and the stirring.

After three hours, analysis of a sample by vapour phase chromatography showed that the ethyl lactate had completely disappeared. The reaction medium was then neutralised under agitation with sodium bicarbonate, then decanted. After washing with an aqueous solution of 50.4 g of sodium sulphite in 500 g of water, the organic phase was concentrated and the residual oil distilled under 80 mbar pressure. 372 g (3.2 mole) ethyl pyruvate was isolated, i.e. a yield of 80.2% of theory calculated with respect to ethyl lactate.

EXAMPLE 2

The process of example 1 was repeated using methyl lactate. A 72% yield of methyl pyruvate was isolated.

EXAMPLE 3

The process of example 1 was repeated using butyl lactate. An 88% yield of pure butyle pyruvate was isolated.

EXAMPLE 4

The process of example 1 was repeated in daylight, in the absence of the illumination provided by the incandescent lamp. Complete disappearance of the ethyl lactate took six hours following addition of the hydrogen peroxide. After treatment, a yield of 80% of theory of ethyl pyruvate was isolated.

EXAMPLE 5

The process of example 1 was repeated in complete darkness and the reaction medium left for 10 hours at 25° C. in darkness and under agitation.

After treatment, a yield of 80% of theory of ethyl pyruvate was isolated.

The present invention has been described by way of illustration only and the description is in no way limiting. Any reasonable modification may be made by way of substitution of equivalent means without departing from the scope of the invention.

We claim:

1. In a process for the manufacture of alkyl pyruvates having the general formula:

$$CH_3-CO-COOR$$

wherein R represents a $C_1$-$C_8$ alkyl radical, by oxidation of the corresponding alkyl lactate, the improvement comprising;

admixing a 30 to 70% by weight aqueous hydrogen peroxide solution into a solution of the alkyl lactate in an organic water-immiscible solvent containing a catalytic quantity of bromine while maintaining a temperature of 15°-30° C.

2. The process according to claim 1 wherein the molar ratio of hydrogen peroxide to alkyl lactate is between 1 and 1.2.

3. The process according to claim 1 wherein said catalytic quantity of bromine is between 10 and 200 mmoles per mole of alkyl lactate employed.

4. The process according to claim 1 wherein said process is carried out in dichloromethane.

5. The process according to claim 1 wherein said process is carried out in the presence of visible or near ultraviolet radiation of wavelengths between 250 nm and 700 nm.

6. The process according to claim 1 wherein the organic solvent is selected from the group consisting of water immiscible dichloromethane, 1,1,1-trichloroethane, and chlorobenzene.

* * * * *